United States Patent [19]

Hosoi

[11] Patent Number: 5,894,339
[45] Date of Patent: Apr. 13, 1999

[54] APPARATUS FOR PRESENTING A TEST CHART

[75] Inventor: Yoshinobu Hosoi, Gamagori, Japan

[73] Assignee: Nidek Co., Ltd., Japan

[21] Appl. No.: 09/048,782

[22] Filed: Mar. 27, 1998

[30] Foreign Application Priority Data

Mar. 31, 1997 [JP] Japan ................... 9-098216

[51] Int. Cl.$^6$ ..................... A61B 3/02
[52] U.S. Cl. ............................ 351/239
[58] Field of Search ................. 351/223, 239, 351/240, 241, 242, 243, 244

[56] References Cited

U.S. PATENT DOCUMENTS 5,416,540  5/1995  Hayashi ................... 351/239
5,444,504  8/1995  Kobayashi et al. ........ 351/237
5,589,897  12/1996 Sinclair et al. ........... 351/223

*Primary Examiner*—George Manuel
*Attorney, Agent, or Firm*—Finnegan, Henderson, Farabow, Garrett & Dunner, L.L.P.

[57] ABSTRACT

An apparatus for presenting a test chart for testing a visual performance of an eye to be examined, the apparatus comprising a test chart plate including a plurality of test chart pictures provided with a plurality of test charts, and with information about the test charts provided between each test chart picture and the next test chart picture, a case having an opening which is approximately the same size as the test chart picture, and a change-over device for moving the desired test chart picture to the opening of the case.

13 Claims, 4 Drawing Sheets

APPARATUS FOR PRESENTING A TEST CHART

BACKGROUND OF THE INVENTION

1. Field of the Invention

The present invention relates to an apparatus for presenting a test chart, which presents a test chart used for testing a visual performance, and more particularly to an apparatus for presenting a test chart suitable for a test in near vision.

2. Description of Related Art

In a visual performance test for a refractive power of an eye to be examined or the like, an apparatus for presenting a test chart, which presents various kinds of test charts, is used, such apparatus is classified into an apparatus for far vision and an apparatus for near vision.

The apparatus for near vision commonly has a simple construction, for example, such apparatus is known that holds a plate in the shape of a disk, which is provided with a plurality of test charts, in a case in the shape of a plate, which is provided with a test chart window, so that the plate may rotate. Referring to the apparatus, if an operator rotates the plate by operating, then the test charts are changed-over and placed in the test chart window.

The operator has to understand details of the test charts and the method of use thereof prior to a test in order to test accurately, however, the test chart differs with manufacturers or type of the apparatus, therefore, it is difficult for the operator to memorize all of them. However, if the test is performed with confirming a manual, a guide book or the like, then it takes much time and disables the operator for smooth test. Further, if the operator loses the manuals or the like, then hindrance may be occurred in the case of an unskilled operator not understanding details of test charts sufficiently.

In addition, there is known such apparatus that has a plate provided with a character denoting its testing distance, as well as test charts, peripherally, however, this character is unnecessary for presentation to the examinee. Moreover, if the examinee gaze at the character, then the eye of the examinee is not fixed to a certain point, as a result, it takes much time to perform the test.

SUMMARY OF THE INVENTION

The present invention has been made in view of the above circumstances and has an object to overcome the above problems and to provide an apparatus for presenting a test chart, by which the operator can understand information such as the method of use of test charts or the like, and by which the operator can perform the test smoothly.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, the apparatus of the present invention for presenting a test chart for testing visual performance of an eye to be examined, comprises a test chart plate which is in the shape of a disk and includes a plurality of test-chart pictures provided with test charts, and a test-chart information part arranged between at least one of the test-chart pictures and another of the test-chart pictures, and provided with information about a test chart, a case for rotatably holding the test chart plate and having a window which is approximately the same size as a test-chart picture for viewing by an eye to be examined, and means for rotating the test chart plate to move the desired test-chart picture to the window of the case.

And another aspect of the present invention, an apparatus for presenting a test chart comprises a case having a window for presenting a test chart to an eye to be examined, and a test chart plate being disposed so as to rotate and disposed so that a portion thereof sticks out from one side of the case, wherein the test chart plate includes a plurality of test-chart picture fields provided with test charts along a rotation direction, a field between each test-chart picture field and the next test-chart picture field is provided with an information-display field including information of test charts of the each test-chart picture field.

According to the present invention, it is capable of understanding necessary information, such as details of respective test charts, the method of use, or the like, easily. In addition, the information is made to be covered by the case so that the eye to be examined may not see the information during a test, enabling the accurate test to be performed smoothly.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
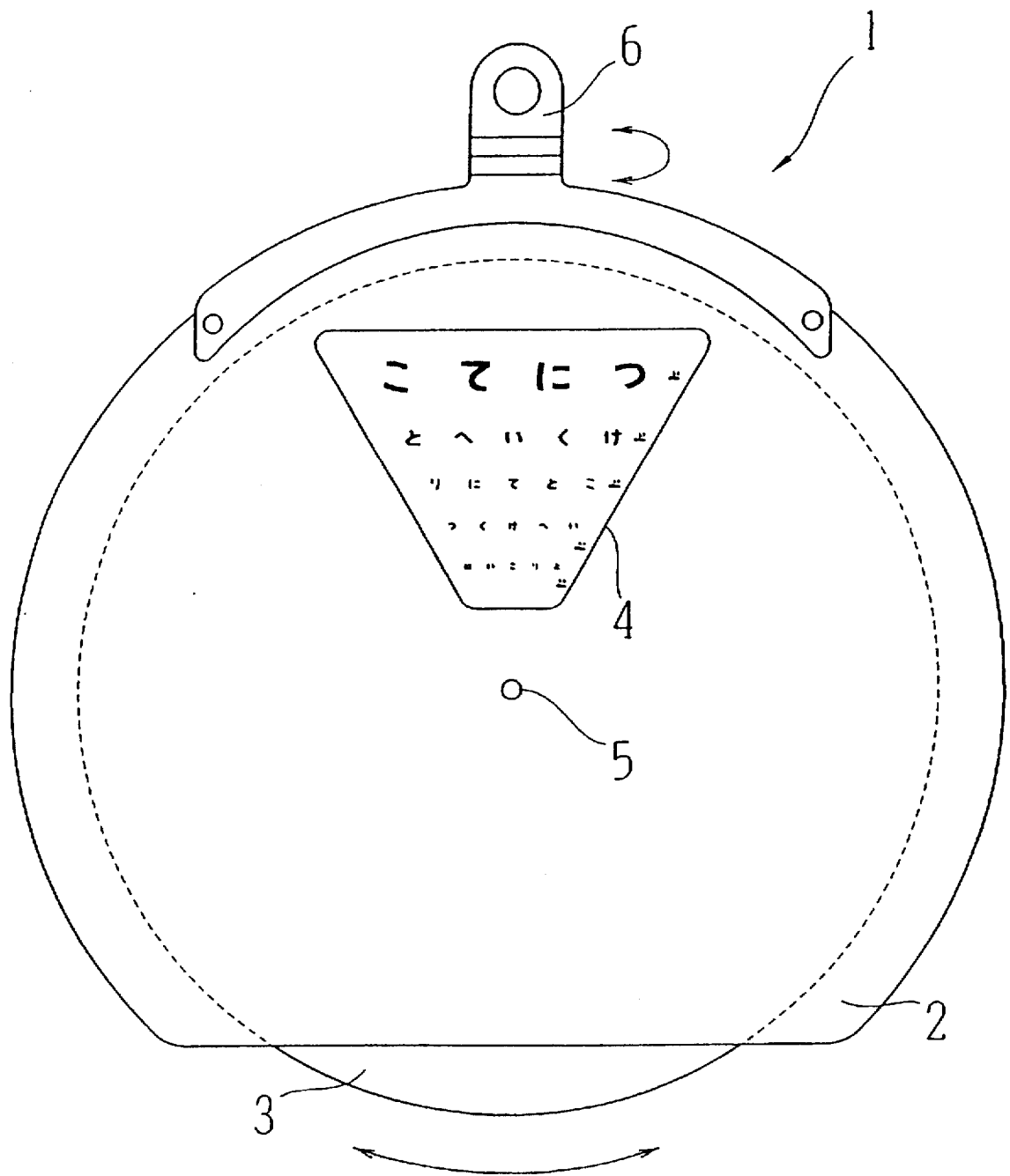
FIG. 1 is an overview showing a schematic configuration of an apparatus for presenting a test chart of the preferred embodiment of the present invention.

A detailed description of one preferred embodiment of an apparatus for presenting a test chart embodying the present invention will now be given referring to the accompanying drawings. FIG. 1 shows an overview of an apparatus 1 for presenting a test chart which is used for a test of near vision. Reference numeral 2 is a case in the shape of a plate, which holds a test chart plate 3 in the shape of a disk, which is provided with a plurality of test charts (a detail of test charts is mentioned below), numeral 4 is a test chart window, having an opening, which is used for presenting a test chart provided for the test chart plate 3 to an eye to be examined. The test chart plate 3 is held by the case 2 so as to rotate with the center at a pin 5, therefore if the operator operates and rotates below portion of the test chart plate 3 which is sticking out from the case 2, then it is changed-over to the desired test chart to be positioned at the test chart window 4. In addition, the test chart window 4 is also provided for just a back side of the case 2 so that test charts provided for the back side of the test chart plate 3 can be presented.

Figure 2:
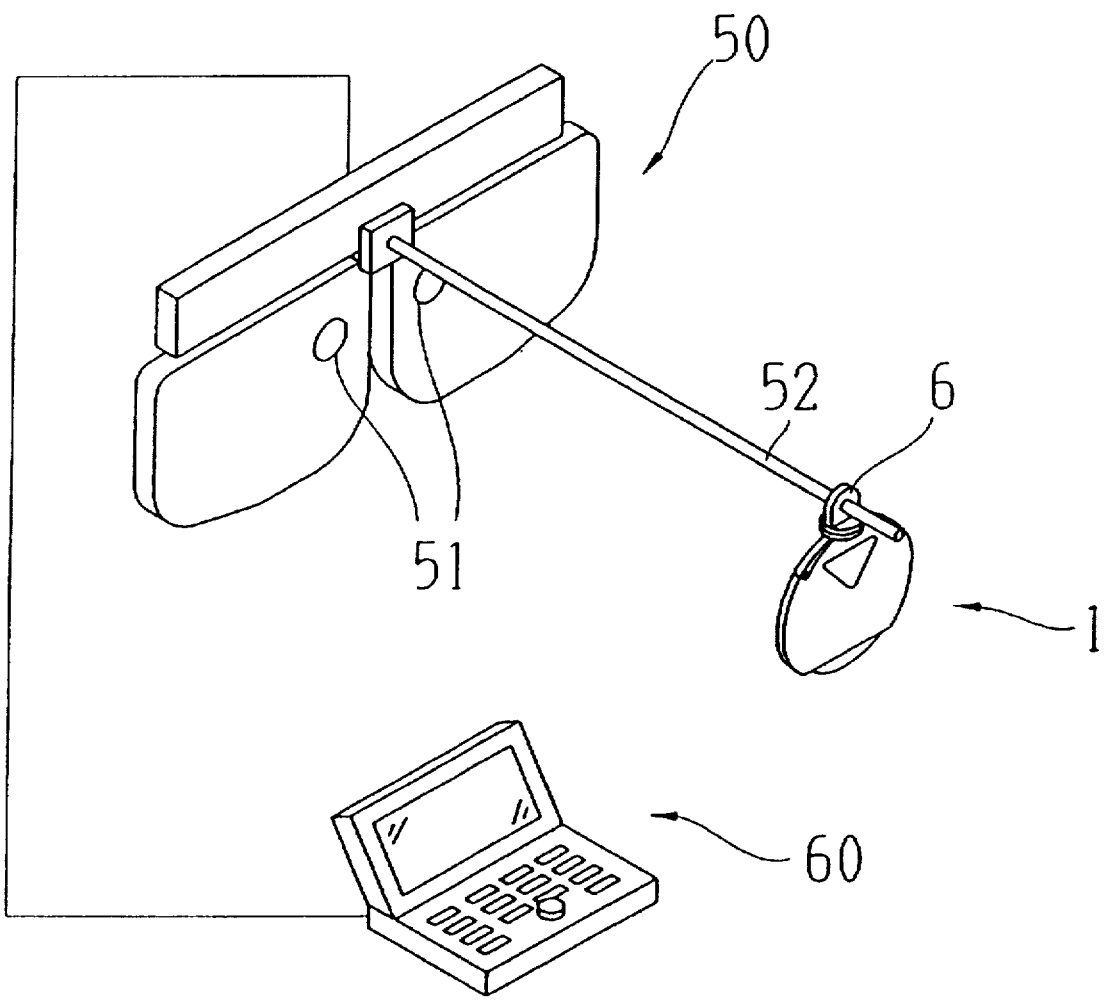
FIG. 2 is a view showing a condition at the time of using the apparatus for presenting a test chart of the preferred embodiment of the present invention by mounting to the subjective refractive power measuring unit.

The apparatus 1 for presenting a test chart, as shown in FIG. 2, can be mounted to the subjective refractive power measuring unit 50 which changes-over various optical elements to be positioned at a test window 51, through the near-point rod 52. The case 2 of the apparatus 1 is provided with a suspending part 6 through which the near-point rod 52 mounted to the subjective refractive power measuring unit 50 is made to pass. The suspending part 6 is movable along the near-point rod 52. The near-point rod 52 has a scale which denotes a test distance. If the suspending part 6 is made to be positioned in accordance with the scale, then a test distance of the apparatus 1 can be set so as to be a desired distance. The case 2 is held by the suspending part 6 so as to rotate, therefore, a test chart provided for the back side thereof can be presented by reversing the case 2 with being suspended. In FIG. 2, reference numeral 60 is an operating unit provided with various switches used for driving the subjective refractive power measuring unit 50.

Figure 3:
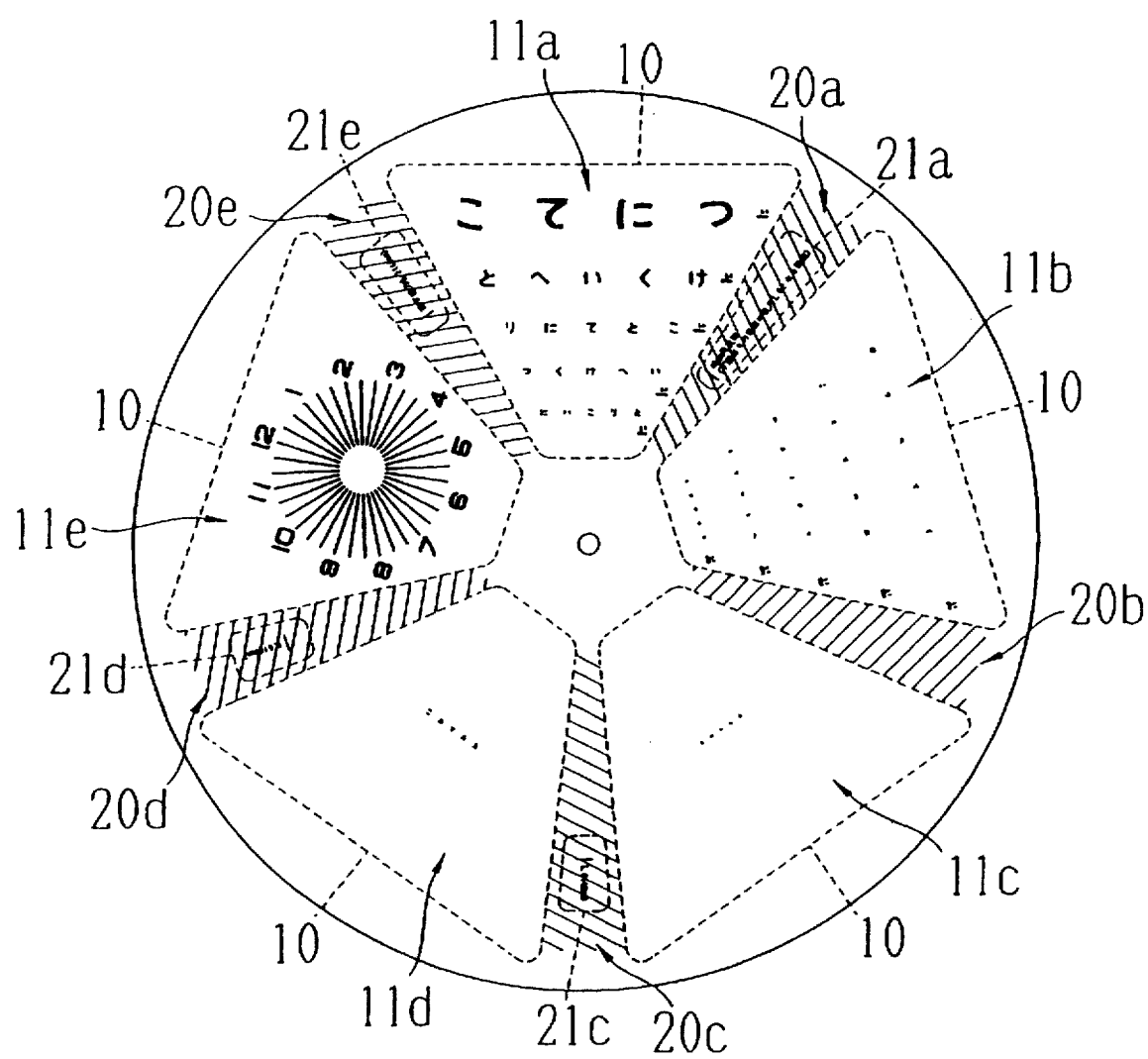
FIG. 3 is a view for illustrating a test chart plate in detail.

Next, the test chart plate 3 will be described hereinafter. In FIG. 3, a dotted line 10 denotes a field corresponding to the test chart window 4 of the case 2, a plurality of test charts in the dotted line 10 is presented to the eye. In the preferred embodiment, five test-charts groups 11a–11e are provided for one side. The test-charts group 11a includes test charts for visual acuity values 0.1–0.5 in a test distance 40 cm, and in the same manner, the test-charts group 11b includes test charts for visual acuity values 0.6–1.0 in a test distance 40 cm. By the side of respective horizontal lines of test charts, there is shown each visual acuity value of respective horizontal lines of test charts in a test distance 40 cm and each distance in which respective horizontal lines of test charts correspond to a visual acuity value 1.0 (see FIG. 4). The test-charts groups 11c and 11d include test charts lined transversely which is utilized for a phoria test, the test-charts group 11c is drawn to be a size corresponding to a visual acuity value 1.0 in a test distance 40 cm, and the test-charts group 11d is drawn to be a size corresponding to a visual acuity value 0.6 in a test distance 40 cm, respectively. The test-charts group 11e is a radial test chart in which numerals around radial lines are drawn to be a size corresponding to a visual acuity value 0.2 in a test distance 40 cm.

Figure 4:
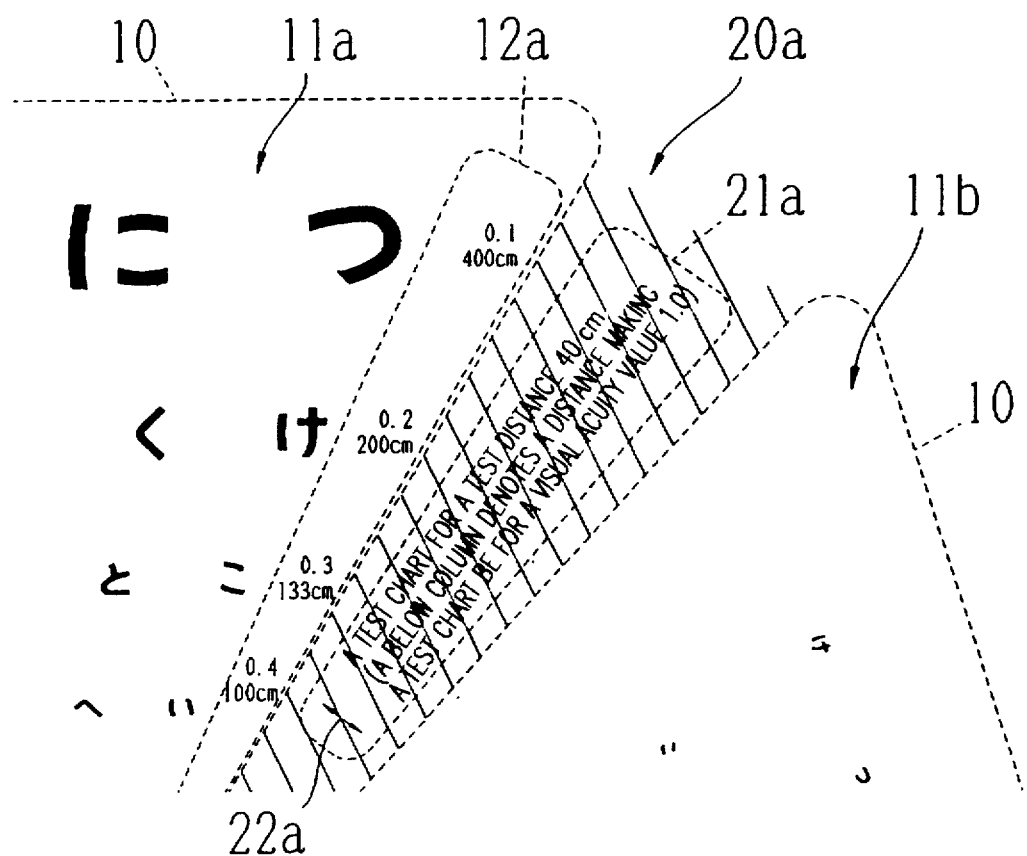
FIG. 4 is a view showing an information-display part next to a test chart for visual acuity test in detail.

In FIG. 3, fields 20a–20e denoted by oblique lines between respective dotted lines 10s are covered by the case 2 during the test so as not to be seen through the test chart window 4. These fields 20a–20e are provided with information-display parts 21a and 21c–21e, in which a test distance, the method of use or the like for respective test-charts groups 11a–11e are drawn. For example, in the information-display part 21a, as shown in FIG. 4, information concerning the test-charts groups 11a and 11b are drawn, namely, such description "both test-charts groups are for a test distance 40 cm" is drawn. Further, below column of the display 12a where is at the side of respective horizontal lines of test charts, there is shown a description denoting a distance making the test chart be for a visual acuity value 1.0. In addition, an arrow 22a shows that contents of the information-display part 21a means the test-charts groups 11a and 11b next to there.

The information-display part 21c shows a test distance of the test-charts group 11c and the matter that the test-charts group 11c is for a visual acuityvalue 1.0 in the test distance, and the information-display part 21d shows a test distance of the test-charts group 11d and a visual acuity value in the test distance. The information-display part 21e shows a test distance of the test-charts group 11e and the matter that the numeral is for a visual acuity value 0.2 in the test distance. The information-display parts 21c–21e are also turned out by arrows, respectively.

Figure 5:
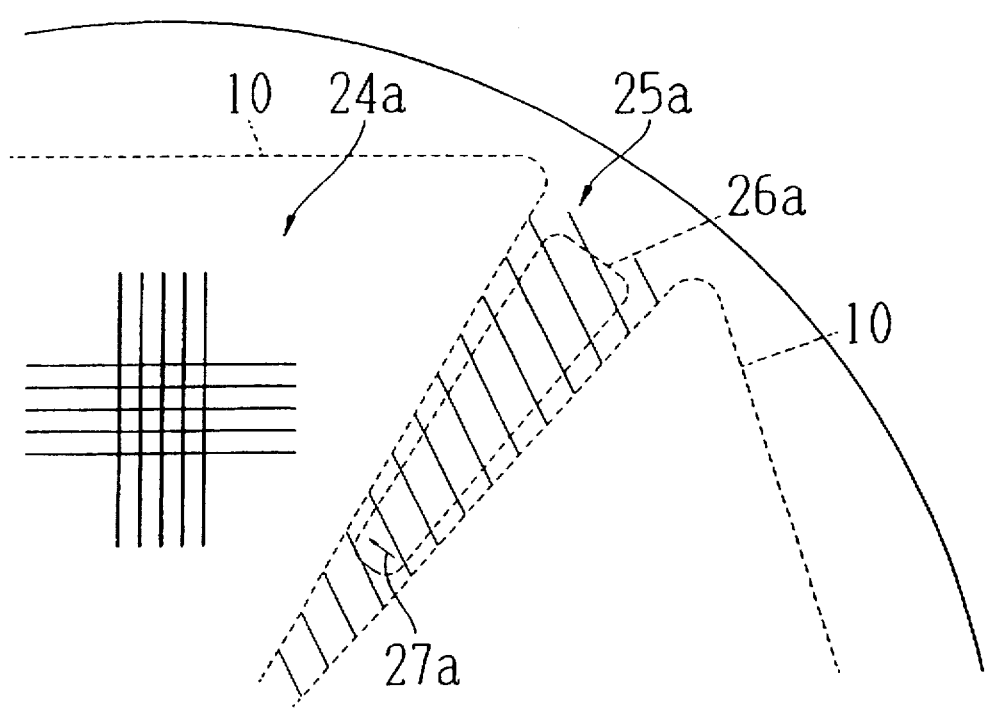
FIG. 5 is a view showing an example of test charts provided for a back side of the test chart plate.

In addition, the back side of the test chart plate 3 is also provided with five test-charts groups different from the ones shown in FIG. 3, and the information-display parts concerning each test-charts group in the field where do not appear on the test chart window 4 during test. FIG. 5 shows an example thereof, and inside of the dotted line 10 corresponding to the test chart window 4 is provided with a cross grid test chart 24a which is utilized for testing a presbyopia adding power (diopter). And, for the field 25a which exists between the cross grid test chart 24a and the next test chart on the right side, an information-display part 26a for the cross grid test chart 24a is provided, and is denoted by an arrow 27a. The information is, for example, related to the method of use of the cross grid test chart 24a such as "Set a cross cylinder lens then add a plus power (diopter) until an examinee can see both vertical lines and horizontal lines equally.".

Next, a test of the preferred embodiment will be described hereinafter by utilizing such apparatus 1 for presenting a test chart having such composition. Firstly, a test for detecting a presbyopia adding power (diopter) will be described. After a test for far vision is performed by using the subjective refractive power measuring unit 50, as shown in FIG. 2, the apparatus 1 for presenting a test chart, mounted to the near-point rod 52, is set ahead of the test window 51, then above-mentioned cross grid test chart 24a is made to be positioned at the test chart window 4. Besides, a test distance for cross grid test is not defined, however, the test distance may be preferably set so as to be 40 cm considering the visual acuity test to be performed thereafter. In the case that the operator want to know a test distance for a visual acuity test, the operator can confirm it by rotating and operating the test chart plate 3 to be appeared on the information-display part 21a. In addition, in the case that the operator want to know the method of use of the cross grid test chart 24a, the operator can confirm it by making the information-display part 26a appear on the test chart window 4 in the same manner.

The operator sets the optical system corresponding to the perfect correcting power values for both eyes, obtained by the far vision test, to the test window 51 of the subjective refractive power measuring unit 50 by operating the operating part 60, then sets a cross cylinder lens. And, the operator adds a plus spherical power (diopter) until the examinee can see both vertical and horizontal lines of the cross grid test chart 24a equally, obtaining a desired adding power (diopter).

Next, a visual acuity test of near vision will be described. The apparatus 1 for presenting a test chart is mounted to the subjective refractive power measuring unit 50 through the near-point rod 52, and either test-charts group 11a or 11b is positioned at the test chart window 4 so as to be presented to the eye. In the case that the operator want to know a test distance in order to set this test chart, the operator can confirm it by seeing the information-display part 21a. In addition, in the case of performing a test with different test distance, the operator can understand details of distance display drawn on the side of respective horizontal lines of test-charts groups 11a and 11b, accordingly, the operator can perform the test in order to examine whether a visual acuityvalue 1.0 is obtained or not by making the apparatus 1 for presenting a test chart be positioned at its distance.

As described above, for the test chart plate 3, since the information necessary for test concerning each test-charts group is provided, therefore the operator can confirm the information easily prior to the presentation of the test-charts group to the examinee without preparing a manual, a guide book or the like. In addition, during a test, since the information does not appear on the test chart window 4, therefore, the unnecessary characters are made not to presented to the eye, accordingly the accurate test can be performed without the eye being unfixed.

Besides, if a method of use of respective test charts and a simplified summary are provided for the information-display parts 21c, 21d and 21e, then it becomes more convenient. For example, if the method of use such as "Add the plus spherical power (diopter) to make the numeral readable. Multiply the numeral of darker lines by 30 to obtain the astigmatism axial angle" is drawn on the information-display part 21e for radial test charts, thereby the operator is to be assisted.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is the claimed is:

1. An apparatus for presenting a test chart comprising:

a case having a window for presenting the test chart to an eye to be examined, and an opening; and a test chart plate disposed in the case to rotate and disposed so that a portion of the test chart plate is exposed at the opening in the case;

wherein said test chart plate includes a plurality of test-chart picture fields provided with different test charts along a rotation direction, and an information-display field provided with information of the test charts, the information-display field arranged between one of the test-chart picture fields and another of the test-chart picture fields.

2. The apparatus according to claim 1, wherein the information of the test chart provided for said information-display field includes information concerning a test distance of the test chart or information concerning the test distance and a visual acuity value of the test chart.

3. The apparatus according to claim 1, wherein the information of the test chart provided for said information-display field includes information concerning how to use the test chart.

4. The apparatus according to claim 1, wherein said information-display field is covered by said case under the condition where a test-chart picture field is presented to the eye.

5. The apparatus according to claim 1, wherein one of the test charts provided for said test-chart picture fields includes a test chart for near vision.

6. The apparatus according to claim 5, wherein one of the test charts provided for said test-chart picture fields further includes a cross grid test chart for testing a presbyopia adding power.

7. The apparatus according to claim 1, wherein said test-chart picture fields and said information-display fields can be rotated at will and presented at said window, by making said test chart plate rotate by contacting the portion of said test chart plate exposed at the opening of said case.

8. An apparatus for presenting a test chart comprising:

a case having a window for presenting the test chart to an eye to be examined; and a test chart plate disposed in said case so as to rotate;

said test chart plate including a plurality of test-chart picture fields provided with different test charts along a rotational direction and an information-display field provided with information of the test chart, the information-display field being arranged between one of the test-chart picture fields and another of the test-chart picture fields.

9. The apparatus according to claim 8, wherein said test chart plate is being disposed in said case so that a portion of said test chart plate protrudes from said case.

10. The apparatus according to claim 9, wherein said case has an opening from which the portion of said test chart plate protrudes.

11. An apparatus for presenting a test chart for testing visual performance of an eye to be examined, the apparatus comprising:

a test chart plate which is in the shape of a disk and includes a plurality of test-chart pictures provided with test charts, and a test-chart information part arranged between at least one of the test-chart pictures and another of the test-chart pictures, and provided with information about a test chart;

a case for rotatably holding the test chart plate and having a window which is approximately the same size as a test-chart picture for viewing by an eye to be examined; and means for rotating the test chart plate to move the desired test-chart picture to the window of said case.

12. The apparatus according to claim 11, for presenting a test chart for near vision, wherein the information provided in the test chart information part includes a test distance concerning the test chart or both the test distance and a visual acuity value concerning the test chart.

13. The apparatus according to claim 11, for presenting a test chart for near vision, wherein the information provided in the test chart information part includes a method of use concerning the test chart.

* * * * *